United States Patent
Maeda et al.

(10) Patent No.: US 7,432,035 B2
(45) Date of Patent: *Oct. 7, 2008

(54) (METH)ACRYLATE DERIVATIVE, POLYMER AND PHOTORESIST COMPOSITION HAVING LACTONE STRUCTURE, AND METHOD FOR FORMING PATTERN BY USING IT

(75) Inventors: Katsumi Maeda, Tokyo (JP); Shigeyuki Iwasa, Tokyo (JP); Kaichiro Nakano, Tokyo (JP); Etsuo Hasegawa, Tokyo (JP)

(73) Assignee: NEC Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/713,791

(22) Filed: Mar. 5, 2007

(65) Prior Publication Data

US 2007/0218403 A1    Sep. 20, 2007

Related U.S. Application Data

(63) Continuation of application No. 09/750,116, filed on Dec. 29, 2000, now Pat. No. 7,186,495, which is a continuation-in-part of application No. PCT/JP99/03580, filed on Jul. 2, 1999.

(30) Foreign Application Priority Data

| Jul. 3, 1998 | (JP) | 1998/188853 |
| Nov. 18, 1998 | (JP) | 1998/328491 |

(51) Int. Cl.
*G03F 7/00*    (2006.01)
*G03F 7/004*   (2006.01)

(52) U.S. Cl. .............. 430/270.1; 430/281.1

(58) Field of Classification Search ........... 430/281.1, 430/270.1
See application file for complete search history.

(56) References Cited

U.S. PATENT DOCUMENTS

| 4,018,767 | A | 4/1977 | Buyniski et al. |
| 4,166,915 | A | 9/1979 | Buchholz |
| 4,188,219 | A | 2/1980 | Cawley |
| 5,185,143 | A | 2/1993 | Cohen |
| 5,541,344 | A | 7/1996 | Becker et al. |
| 5,811,462 | A | 9/1998 | Hungate |
| 5,919,598 | A | 7/1999 | Flaim et al. |
| 6,008,306 | A | 12/1999 | Hafner et al. |
| 6,057,083 | A | 5/2000 | Taylor et al. |
| 6,074,801 | A | 6/2000 | Iwasa et al. |
| 6,165,680 | A | 12/2000 | Choi |
| 6,280,898 | B1 | 8/2001 | Hasegawa et al. |
| 6,303,266 | B1 | 10/2001 | Okino et al. |
| 6,319,655 | B1 | 11/2001 | Wong et al. |
| 6,383,713 | B1 | 5/2002 | Uetani et al. |
| 6,391,521 | B1 | 5/2002 | Ito et al. |
| 6,406,828 | B1 | 6/2002 | Szmanda et al. |
| 6,410,204 | B1 | 6/2002 | Kodama et al. |
| 6,426,171 | B1 | 7/2002 | Jung et al. |
| 6,441,115 | B1 | 8/2002 | Chang et al. |
| 6,444,396 | B1 | 9/2002 | Watanabe et al. |
| 6,447,980 | B1 | 9/2002 | Rahman et al. |
| 6,461,788 | B1 | 10/2002 | Miwa et al. |
| 6,462,158 | B1 * | 10/2002 | Miwa et al. ............. 526/282 |
| 6,482,568 | B1 | 11/2002 | Douki et al. |
| 6,517,994 | B2 | 2/2003 | Watanabe |
| 6,524,765 | B1 | 2/2003 | Nishi et al. |
| 6,548,220 | B2 * | 4/2003 | Uetani et al. ............ 430/270.1 |
| 6,579,659 | B2 * | 6/2003 | Uetani et al. ............ 430/270.1 |
| 6,596,458 | B1 | 7/2003 | Sato et al. |
| 6,639,035 | B1 | 10/2003 | Chen et al. |
| 6,680,159 | B2 | 1/2004 | Barclay et al. |
| 6,703,178 | B2 | 3/2004 | Chen et al. |
| 6,720,430 | B2 | 4/2004 | Chen et al. |
| 6,746,818 | B2 | 6/2004 | Kinsho et al. |
| 6,759,176 | B2 | 7/2004 | Iwai et al. |
| 6,764,811 | B2 | 7/2004 | Endo et al. |
| 6,787,282 | B2 * | 9/2004 | Sato .................... 430/170 |
| 6,808,860 | B2 | 10/2004 | Sato et al. |
| 6,808,862 | B2 | 10/2004 | Kodama |
| 6,830,866 | B2 | 12/2004 | Kobayashi et al. |
| 6,835,524 | B2 | 12/2004 | Hatakeyama et al. |
| 6,835,527 | B2 | 12/2004 | Takata et al. |

| | | |
|---|---|---|
| 6,844,133 B2 | 1/2005 | Nishi et al. |

FOREIGN PATENT DOCUMENTS

| | | | |
|---|---|---|---|
| JP | 2-027660 | | 6/1990 |
| JP | 5-134416 | | 6/1993 |
| JP | 7-028237 | | 1/1995 |
| JP | 7-199467 | | 8/1995 |
| JP | 7-219231 | | 8/1995 |
| JP | 7-234511 | | 9/1995 |
| JP | 7-252324 | | 10/1995 |
| JP | 8-015865 | | 1/1996 |
| JP | 8-259626 | | 10/1996 |
| JP | 8-335603 | | 12/1996 |
| JP | 10-003169 | | 1/1998 |
| JP | 10-171122 | | 6/1998 |
| JP | 2002251013 A | * | 9/2002 |
| JP | 2002357905 A | * | 12/2002 |
| JP | 2003057825 A | * | 2/2003 |
| JP | 2003057905 A | * | 2/2003 |
| JP | 2003122007 A | * | 4/2003 |

OTHER PUBLICATIONS

Answer 1 of 7 Registry Copyright 2005 ACS on STN, Compound RN 61380-96-9.

Answer 4 of 7 Registry Copyright 2005 ACS on STN, Compound RN 61380-96-9.

R. D. Allen et al., "Progress In 193 nm Positive Resists," Journal of Photopolymer Science and Technology, vol. 9, No. 3, pp. 456-474, 1996.

R. D. Allen et al., "Resolution And Etch Resistance Of A Family Of 193 Nm Positive Resists," Journal of Photopolymer Science and Technology, vol. 8, No. 4, pp. 623-636, 1995.

S. Bechmann et al., "Zur Kenntnis der dei der Hydratisierung von Biclyclo-[1.2.2]-hepten-carbonsauren entstehenden Lactone," Chem. Ber., vol. 94, 48-58, 1961.

J. V. Crivello et al., "A New Preparation of Triarylsulfonium and -selenonium Salts via the Copper (II)-Catalyzed Arylation of Sulfides and Selenides with Diaryliodonium Salts," Journal of the Organic Chemistry, vol. 43:15, pp. 3055-3085, 1978.

H. B. Henbest et al., "Aspects of Stereochemistry," J. Chem. Soc., pp. 221-226, 1959.

F. M. Houlihan et al., "The Synthesis Characterization and Lithography of x-Substituted 2-Nitrobenzyl Arylsufonate Photo-Acid Generators with Improved Resistance to Post Exposure Bake," SPIE Proceedings, vol. 2195, pp. 137-151, 1994.

D. C. Hofer et al., "193 nm Photoresist R&D: The Risk & Challenge," Journal of Photopolymer Science and Technology, vol. 9:3, pp. 387-397, May 16, 1996.

H. Ito et al., "Applications of Photoinitiators to the Design of Resists for Semiconductor Manufacturing," American Chemical Society Symposium Series, vol. 242, pp. 11-23, 1984.

R. M. Moriarty et al., "(IV) Acetate Oxidation of Unsaturated Carboxylic Acids, Esters and Amides. The Mechanism of the Reaction," Tetrahedron Letters No. 38, pp. 4363-4367, 1966, Pergamon Press, Ltd., printed in Great Britain.

K. C. Ramey, "Analysis of the Nuclear Magnetic Resonance Spectra of Some 2,6-Bridged Bicyclo[2.2.1]heptane Derivatives," Journal of the American Chemical Society, vol. 89:10, 1987.

Takechi et al., "Alicyclic Polymer for ArF and KrF Excimer Resist Based on Chemical Amplification," Journal of Photopolymer Science and Technology, vol. 5:3, pp. 439-446, 1992.

T. Ueno et al., "Chemical Amplification Positive Resist Systems Using Novel Sulfonates as Acid Generators," Proceeding of PME 1989, Kodansha, pp. 413-424, 1990.

* cited by examiner

*Primary Examiner*—Amanda C. Walke
(74) *Attorney, Agent, or Firm*—Foley & Lardner LLP

(57) ABSTRACT

There are here disclosed a photoresist material for lithography using a light of 220 nm or less which comprises at least a polymer represented by the following formula (2) and a photo-acid generator for generating an acid by exposure:

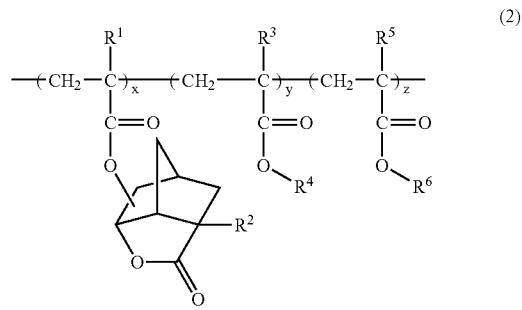

wherein $R^1$, $R^2$, $R^3$ and $R^5$ are each a hydrogen atom or a methyl group; $R^4$ is an acid-labile group, an alicyclic hydrocarbon group having 7 to 13 carbon atoms, which has an acid labile group, an alicyclic hydrocarbon group having 7 to 13 carbon atoms, which has a carboxyl group, or a hydrocarbon group having 3 to 13 carbon atoms, which has an epoxy group; $R^6$ is a hydrogen atom, a hydrocarbon group having 1 to 12 carbon atoms, or an alicyclic hydrocarbon group having 7 to 13 carbon atoms, which has a carboxyl group; x, y and z are optional values which meet $x+y+z=1$, $0<x\leq 1$, $0\leq y<1$ and $0\leq z<1$; and a weight-average molecular weight of the polymer is in the range of 2000 to 200000, and a resin having a (meth)acrylate unit of an alicyclic lactone structure represented by the formula (3):

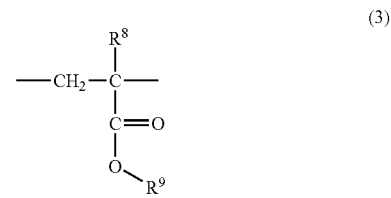

wherein $R^8$ is a hydrogen atom or a methyl group, and $R^9$ is a hydrocarbon group of 7 to 16 carbon atoms having an alicyclic lactone structure.

11 Claims, 1 Drawing Sheet

(METH)ACRYLATE DERIVATIVE, POLYMER AND PHOTORESIST COMPOSITION HAVING LACTONE STRUCTURE, AND METHOD FOR FORMING PATTERN BY USING IT

TECHNICAL FIELD

The present invention relates to a novel (meth)acrylate derivative, its polymer, particularly a resin for use in a photoresist material in which a far ultraviolet light having a wavelength of 220 nm or less is used as an exposure light, and a photoresist composition.

BACKGROUND ART

In the field of the manufacture of various electron devices typified by semiconductor devices in which fine working of half-micron order is required, the further increase of density and integration of these devices has been demanded. Therefore, a photolithography technique required for the formation of fine patterns has been more and more strict.

In particular, in the manufacture of DRAMs having an integration degree of 1 gigabit or more in which a working technique of 0.18 μm or less is required, the utilization of photolithography in which an ArF excimer laser (193 nm) is used has been investigated in recent years [Donald C. Hofer et al., "Journal of Photopolymer Science and Technology", Vol. 9, No. 3, p. 387-397 (1996)]. Accordingly, it has been desired to develop a resist material suitable for the photolithography in which the ArF light is used.

In developing this resist for ArF exposure, it is necessary to improve a cost performance of the laser, because a life span of a gas which is a raw material of the laser is short and a laser apparatus itself is expensive. Therefore, high resolution properties suitable for the fine working and the enhancement of sensitivity are strongly desired.

As the resists having a heightened sensitivity, there are well known chemically amplified resists in which a photo-acid generator as a photosensitive material is utilized. For example, as typical examples, resists comprising combinations of triphenylsulfonium hexafluoroarcenate and poly(p-tert-butoxycarbonyloxy-α-methylstyrene) are mentioned in Japanese Patent Application Publication No. 27660/1990. Such chemically amplified resists are now widely used as resists for a KrF excimer laser [e.g., Hiroshi Ito, C. Grant Wilson, "American Chemical Society Symposium Series", Vol. 242, p. 11-23 (1984)]. The chemically amplified resists are characterized in that a proton acid generated from the photo-acid generator as a contained component by light irradiation gives rise to an acid catalytic reaction with a resist resin or the like by a heat treatment after exposure. As understood from the above, in the chemically amplified resist, there can be achieved a much higher sensitivity as compared with a conventional resist having a photoreactive efficiency (a reaction per photon) of less than 1. Nowadays, most of the developed resists are of the chemical amplification type.

However, in the case of the lithography in which a short wavelength light of 220 nm or less typified by an ArF excimer laser is used, the resists for forming fine patterns are required to possess novel characteristics which the conventional material cannot satisfy, i.e., a high transparency to an exposure light of 220 nm or less, and a dry etching resistance.

A conventional photoresist material for g-line (438 nm), i-line (365 nm) or the KrF excimer laser (248 nm) utilizes a resin such as a novolak resin or a poly(p-vinylphenol) in which an aromatic ring is present in a structural unit. The dry etching resistance of this aromatic ring enables the etching resistance of the resin to be maintained. As a negative photoresist material, a crosslinking agent is further added to the resin. Examples of the usable crosslinking agent include azide compounds such as 2,6-di(4'-azidobenzal)-4-methylcyclohexanone and 3,3'-diazidodiphenylsulfone as well as methylolmelamine resins. However, the resin having the aromatic ring extremely strongly absorbs a light having a wavelength of 220 nm or less. Therefore, most of the exposure light is absorbed on the surface of the resist, and so the exposure light cannot reach a substrate, with the result that the fine resist pattern cannot be formed. For this reason, the conventional resin cannot be directly applied to the photolithography in which a short wavelength light of 220 nm or less is used. Accordingly, a photoresist material is now desired which contains no aromatic ring, has the etching resistance, and is transparent to the wavelength light of 220 nm or less.

As polymeric compounds having the transparency to the ArF excimer laser (193 nm) and the dry etching resistance, there have been suggested copolymers each having an adamantyl methacrylate unit which are alicyclic polymers [Takechi et al., "Journal of Photopolymer Science and Technology", Vol. 5, No. 3, p. 439-446 (1992)] and copolymers each having an isobornyl methacrylate unit [R. D. Allen et al., "Journal of Photopolymer Science and Technology", Vol. 8, No. 4, p. 623-636 (1995) and Vol. 9, No. 3, p. 465-474 (1996)].

However, the (meth)acrylate derivative having an alicyclic group which is used in the former resin does not have any polar group having adhesive properties to a substrate (e.g., a carboxyl group or a hydroxyl group). Therefore, a homopolymer of a monomer having the alicyclic group is strongly hydrophobic and poor in the adhesive properties to the substrate to be worked (e.g., a silicon substrate), and so it is difficult to form a homogeneous coating film with a high reproducibility. Furthermore, the former resin does not have a residue capable of expressing a solubility difference before and after exposure in an adamantane-including residue, an isobornyl-including residue or a menthyl-including residue unit having the dry etching resistance, and therefore, any pattern cannot be formed by the exposure. Thus, the former resin can be utilized as the resin component of the positive resist only by forming a copolymer of the former resin itself with a comonomer such as t-butyl methacrylate or a tetrahydropyranyl-methacrylate capable of exerting the solubility difference, or a comonomer such as methacrylic acid having the adhesive properties to the substrate. However, a content of the comonomer is required to be about 50 mol %, and the dry etching resistance per comonomer is noticeably low, so that a dry etching resistance effect by the aliphatic group noticeably deteriorates. Accordingly, the former resin is less practical as the resin having the dry etching resistance.

SUMMARY OF THE INVENTION

Thus, an object of the present invention is to provide a high-sensitive positive and negative photoresist materials having excellent transparency and etching resistance for use in a lithography in which an exposure light having a wavelength of 220 nm or less, in particular, an exposure light of 180 nm to 220 nm is used.

Another object of the present invention is to provide a method for forming a pattern by the use of these photoresist materials.

Still another object of the present invention is to provide a novel (meth)acrylate derivative and polymer for use in these materials.

That is to say, the first aspect of the present invention is directed to positive or negative photoresist materials which comprises at least a polymer composed by copolymerizing (meth)acrylate derivative represented by the formula (1), with polymeric compounds and a photo-acid generator for generating an acid by exposure:

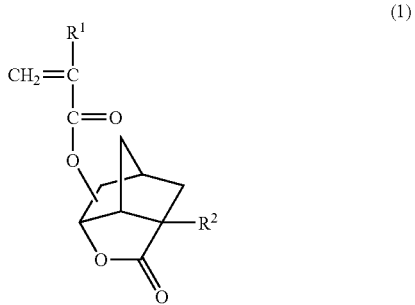

(1)

wherein $R^1$ and $R^2$ are each a hydrogen atom or a methyl group.

As example of these polymer is represented by the following formula (2):

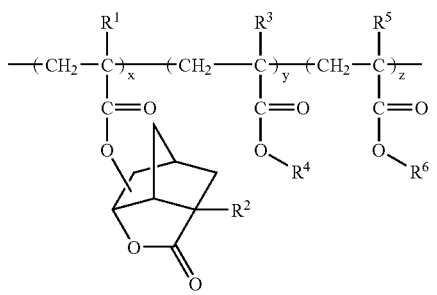

(2)

wherein $R^1$, $R^2$, $R^3$ and $R^5$ are each a hydrogen atom or a methyl group; $R^4$ is an acid-labile group, an alicyclic hydrocarbon group having 7 to 13 carbon atoms, which has an acid-liable group, an alicyclic hydrocarbon group having 7 to 13 carbon atoms, which has a carboxyl group, or a hydrocarbon group having 3 to 13 carbon atoms, which has an epoxy group; $R^6$ is a hydrogen atom, a hydrocarbon group having 1 to 12 carbon atoms, or an alicyclic hydrocarbon group having 7 to 13 carbon atoms, which has a carboxyl group; and x, y and z are optional values which meet x+y+z=1, 0<x≦1, 0≦y<1 and 0≦z<1.

Furthermore, the above-mentioned material may contain a polyhydric alcohol.

The second aspect of the present invention is directed to a method for forming a pattern which comprises a step of applying the above-mentioned photoresist material onto a substrate to be worked, a step of exposing the material to a light having a wavelength of 180 to 220 nm, a step of carrying out baking, and a step of performing development; and the exposure light may be an ArF excimer laser light.

The third aspect of the present invention is directed to the (meth)acrylate derivatives represented by the formula (1) and a polymer composed by copolymerizing (meth)acrylate derivative represented by the formula (1) with polymeric compounds.

The polymer of the present invention is excellent in dry etching resistance and transparency, and the resist material using the polymer of the present invention is excellent in resolution and adhesive properties to the substrate, whereby the formation of a fine pattern necessary to manufacture semiconductor elements is possible.

The fourth aspect of the present invention is directed to a resin for resist characterized in that, in the resin for resist, the solubility to an alkaline aqueous solution of which increases due to the decomposition of an acid-decomposable group thereof by an action of an acid, said resin is the resin for resist_having a (meth)acrylate unit of an alicyclic lactone structure represented by the formula (3), the resin for resist which is obtained by polymerizing a (meth)acrylate derivative represented by the formula (1) with other polymerizable compounds or the resin for resist represented by the formula (2):

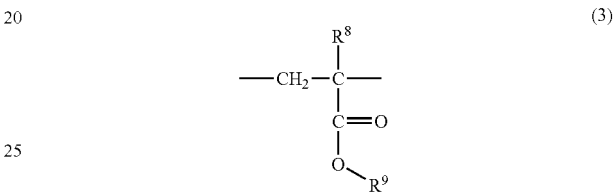

(3)

wherein $R^8$ is a hydrogen atom or a methyl group, and $R^9$ is a hydrocarbon group of 7 to 16 carbon atoms having an alicyclic lactone structure.

Figure 1:
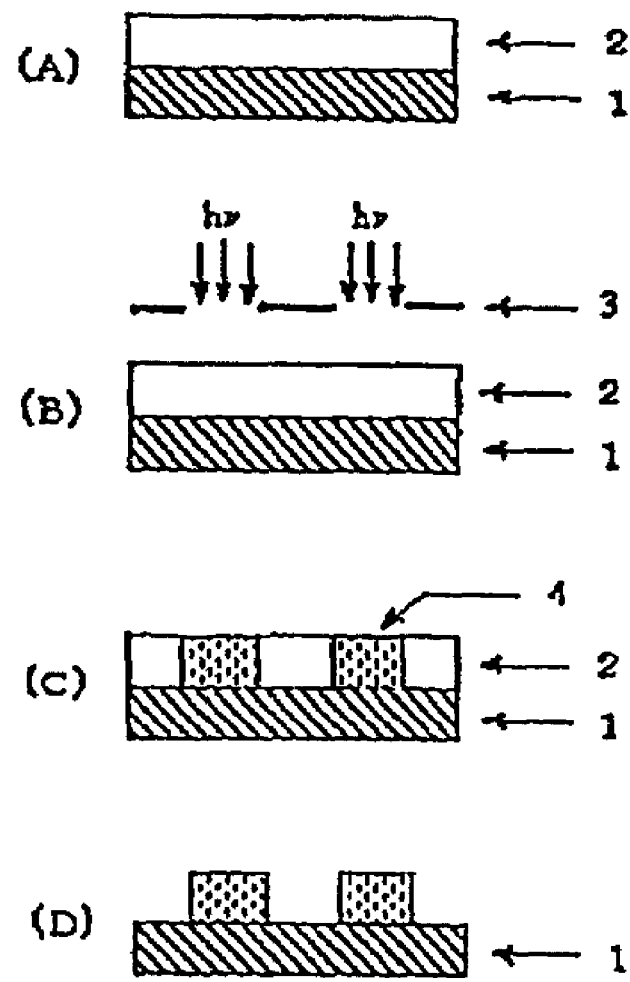
FIGS. 1(A) to 1(D) are sectional views showing a formation procedure of a negative resist pattern of the present invention.

In these drawings:
1 . . . Substrate to be worked
2 . . . Resist film
3 . . . Mask
4 . . . Crosslinked region

DETAILED DESCRIPTION OF THE INVENTION

In the above-mentioned formula (1), $R^1$ and $R^2$ are each a hydrogen atom or a methyl group.

In the above-mentioned formula (2), $R^1$, $R^2$, $R^3$ and $R^5$ are each a hydrogen atom or a methyl group; $R^4$ is an acid-labile group, an alicyclic hydrocarbon group having 7 to 13 carbon atoms, which has an acid-labile group, an alicyclic hydrocarbon group having 7 to 13 carbon atoms, which has a carboxyl group, or a hydrocarbon group having 3 to 13 carbon atoms, which has an epoxy group; $R^6$ is a hydrogen atom, a hydrocarbon group having 1 to 12 carbon atoms, or an alicyclic hydrocarbon group having 7 to 13 carbon atoms, which has a carboxyl group.

Typical examples of the acid-labile group include, but are not limited to, a t-butyl group, a tetrahydropyran-2-yl group, a tetrahydrofuran-2-yl group, a 4-methoxytetrahydropyran-4-yl group, a 1-ethoxyethyl group, a 1-butoxyethyl group, a 1-propoxyethyl group, a 3-oxocyclohexyl group, a 2-methyl-2-adamantyl group, a 8-methyl-8-tricyclo[5.2.1.0$^{2,6}$]decyl group, a 1,2,7,7-tetramethyl-2-norbornyl group, a 2-acetoxymenthyl group, a 2-hydroxymethyl group and a 1-methyl-1-cyclohexylethyl group.

Typical examples of the alicyclic hydrocarbon group having 7 to 13 carbon atoms which has an acid-labile group, alicyclic hydrocarbon group having 7 to 13 carbon atoms which has the carboxyl group include, but are not limited to, a tricyclo[5.2.1.0$^{2,6}$]decylmethyl group, a tricyclo[5.2.1.0$^{2,6}$] decyl group, an adamantyl group, a norbornyl group, a methylnorbornyl group, an isobornyl group, a tetracyclo[4.4.0.1$^{2,5}$.1$^{7,10}$]dodecyl group and a methyltetracyclo[4.4.0.1$^{2,5}$.1$^{7,10}$]dodecyl group having the carboxyl group or an ester group as shown in Table 1.

TABLE 1

| | Chemical Structure of Group |
|---|---|
| Tricyclo[5.2.1.0$^{2,6}$]decylmethyl group having the carboxyl group or the ester group | 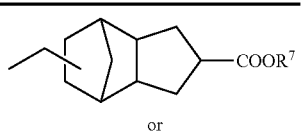 or 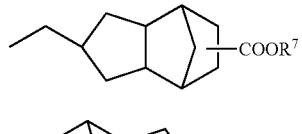 |
| Tricyclo[5.2.1.0$^{2,6}$]decyl group having the carboxyl group or the ester group | 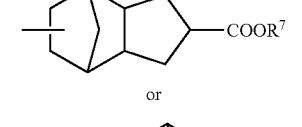 or 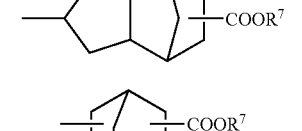 |
| Adamantyl group having the carboxyl group or the ester group | 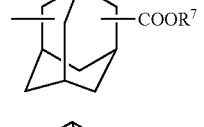 |
| Norbornyl group having the carboxyl group or the ester group | 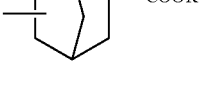 |
| Methylnorbornyl group having the carboxyl group or the ester group | 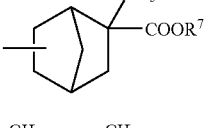 |
| Isobornyl group having the carboxyl group or the ester group | 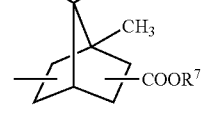 |
| Tetracyclo[4.4.0.1$^{2,5}$.1$^{7,10}$]-dodecyl group having the carboxyl group or the ester group | 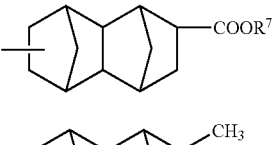 |
| Methyltetracyclo[4.4.0.1$^{2,5}$.1$^{7,10}$]-dodecyl group having the carboxyl group or the ester group |  |

R$^7$ in Table 1 is a hydrogen atom or an acid-labile group, and typical examples of the latter group include, but are not limited to, a t-butyl group, a tetrahydropyran-2-yl group, a tetrahydrofuran-2-yl group, a 4-methoxytetrahydropyran-4-yl group, a 1-ethoxyethyl group, a 1-butoxyethyl group, a 1-propoxyethyl group, a 3-oxocyclohexyl group;, a 2-methyl-2-adamantyl group, a 8-methyl-8-tricyclo[5.2.1.0$^{2,6}$]decyl group, a 1,2,7,7-tetramethyl-2-norbornyl group, a 2-acetoxymenthyl group, a 2-hydroxymenthyl group and a 1-methyl-1-cyclohexylethyl group.

Typical examples of the above-mentioned hydrocarbon group having 3 to 13 carbon atoms which has the epoxy group include, but are not limited to, a glycidyl group, a 3,4-epoxy-1-cyclohexylmethyl group, a 5,6-epoxy-2-norbornyl group, a 5(6)-epoxyethyl-2-norbornyl group, a 5,6-epoxy-2-norbornylmethyl group, a 3,4-epoxytricyclo[5.2.1.0$^{2,6}$]decyl group, a 3,4-epoxytricyclo[5.2.1.0$^{2,6}$]decyloxyethyl group, a 3,4-epoxytetracyclo[4.4.0.1$^{2,5}$.1$^{7,10}$]dodecyl group and a 3,4-epoxytetracyclo[4.4.0.1$^{2,5}$.1$^{7,10}$]dodecylmethyl group as shown in Table 2.

TABLE 2

| R$^4$ | Chemical Structure of Group |
|---|---|
| Glycidyl group | 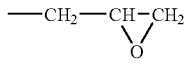 |
| 3,4-Epoxy-1-cyclohexylmethyl group | 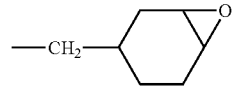 |
| 5,6-Epoxy-2-norbornyl group | 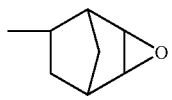 |
| 5(6)-Epoxyethyl-2-norbornyl group | 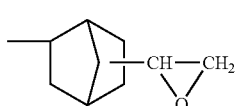 |
| 5,6-Epoxy-2-norbornylmethyl group | 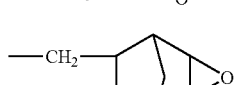 |
| 3,4-Epoxytricyclo [5.2.1.0$^{2,6}$]decyl group | 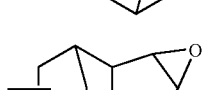 |
| 3,4-Epoxytricyclo [5.2.1.0$^{2,6}$]decyloxyethyl group | 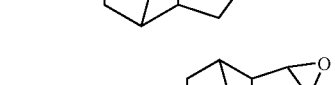 |
| 3,4-Epoxytetracyclo [4.4.0.1$^{2,5}$.1$^{7,10}$]dodecyl group |  |
| 3,4-Epoxytetracyclo [4.4.0.1$^{2,5}$.1$^{7,10}$]dodecylmethyl group | 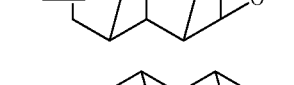 |

Typical examples of the hydrocarbon group having 1 to 12 carbon atoms among the compounds represented by R$^6$ include, but are not limited to, a methyl group, an ethyl group, an n-propyl group, an isopropyl group, an n-butyl group, an isobutyl group, a t-butyl group, a cyclohexyl group, a tricyclo

[5.2.1.0$^{2,6}$]decyl group, an adamantyl group, a norbornyl group, an isobornyl group and a tetracyclo[4.4.0.1$^{2,5}$.1$^{7,10}$]dodecyl group.

Typical examples of the alicyclic hydrocarbon group having 7 to 13 carbon atoms which has the carboxyl group among the compounds represented by R$^6$ include, but are not limited to, a carboxytricyclo[5.2.1.0$^{2,6}$]decylmethyl group, a carboxytricyclo[5.2.1.0$^{2,6}$]decyl group, a carboxyadamantyl group, a carboxynorbornyl group, a carboxymethylnorbornyl group, a carboxyisobornyl group, a carboxytetracyclo[4.4.0.1$^{2,5}$.1$^{7,10}$]dodecyl group and a carboxymethyltetracyclo[4.4.0.1$^{2,5}$.1$^{7,10}$]dodecyl group as shown in Table 3.

TABLE 3

| | Chemical Structure of Group |
|---|---|
| Carboxytricyclo[5.2.1.0$^{2,6}$] decylmethyl group | 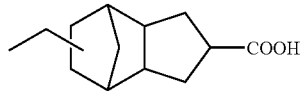 or 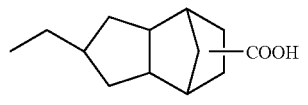 |
| Carboxytricyclo[5.2.1.0$^{2,6}$] decyl group | 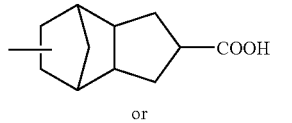 or 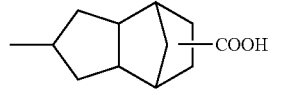 |
| Carboxyadamantyl group | 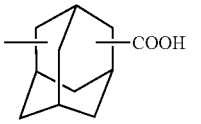 |
| Carboxynorbornyl group | 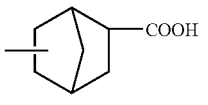 |
| Carboxymethylnorbornyl group | 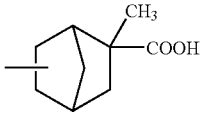 |
| Carboxyisobornyl group | 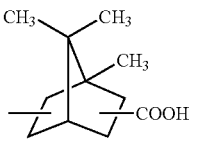 |
| Carboxytetracyclo[4.4.0.1$^{2,5}$.1$^{7,10}$]dodecyl group | 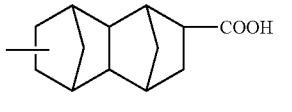 |
| Carboxymethyltetracyclo[4.4.0.1$^{2,5}$.1$^{7,10}$]dodecyl group | 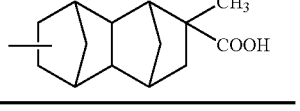 |

Further, in the formula (3), R$^8$ is a hydrogen atom or a methyl group; R$^9$ is a hydrocarbon group of 7 to 16 carbon atoms having an alicyclic lactone structure. Typical examples of the hydrocarbon group of 7 to 16 carbon atoms having an alicyclic lactone structure include, but are not limited to, norbornyl groups having a lactone structure, methylnorbornyl groups having a lactone structure, tetracyclododecyl groups having a lactone structure, methyltetracyclododecyl groups having a lactone structure and adamantyl group having a lactone structure as shown in Table 13.

The resins for resist of the present invention have an alicyclic lactone structure in the structure of the resins, and the characteristic point resides in said lactone structure. Generally, the lactone structure has a higher relative permittivity when compared with an ester structure, an ether structure and an alcohol structure (for example, when compared based on each of the compounds having 4 carbon atoms, a relative permittivity of γ-butylolactone is 39, a relative permittivity of ethyl acetate is 6.02, a relative permittivity of diethyl ether is 4.335, and a relative permittivity of 1-butanole is 17.51 (A Handbook of Chemistry, Fundamental Part II, revised 3rd edition, etc.). As a result, the polarity of the resins having an alicyclic lactone structure in the structure of the resins becomes high, and consequently, the resist which uses the resins for photoresist of the present invention has a superb adhesiveness against a substrate.

Further, since the resins for photoresist of the present invention have not only a lactone structure but also an alicyclic hydrocarbon group, the resins have a superb characteristic of excellent resistance property for dry-etching.

TABLE 13

| | Chemical Structure of R$^9$ |
|---|---|
| Norbornyl group having a lactone structure (1) | 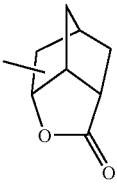 |
| Norbornyl group having a lactone structure (2) | 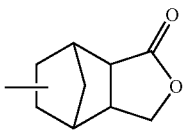 |
| Norbornyl group having a lactone structure (3) | 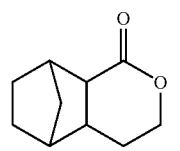 |
| Norbornyl group having a lactone structure (4) | 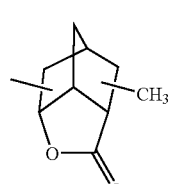 |
| Methylnorbornyl group having a lactone structure (1) | |

TABLE 13-continued

Chemical Structure of R⁹

| Group | Structure |
|---|---|
| Methylnorbornyl group having a lactone structure (2) | |
| Methylnorbornyl group having a lactone structure (3) | |
| Methylnorbornyl group having a lactone structure (4) | |
| Tetracyclododecyl group having a lactone structure (1) | |
| Tetracyclododecyl group having a lactone structure (2) | |
| Tetracyclododecyl group having a lactone structure (3) | |
| Methyltetracyclododecyl group having a lactone structure (1) | |
| Methyltetracyclododecyl group having a lactone structure (2) | |
| Methyltetracyclododecyl group having a lactone structure (3) | |
| Adamantyl group having a lactone structure | |

The polymer which can be used in the present invention can be obtained by subjecting a (meth)acrylate monomer as a raw material to a usual polymerization method such as radical polymerization or ion polymerization. For example, the polymer can be obtained by adding a suitable radical polymerization initiator [e.g., azobisisobutyronitrile (AIBN)] to dry tetrahydrofuran under an inert gas (argon, nitrogen or the like) atmosphere, and then heating and stirring the mixture at 50 to 70° C. for a period of 0.5 to 12 hours. A weight-average molecular weight of the polymer according to the present invention is in the range of 2000 to 200000, more preferably 3000 to 100000. Furthermore, by selecting a feed ratio of the monomer for the copolymer and other polymerization conditions, an optional copolymer can be obtained.

Furthermore, the (meth)acrylate monomer containing the alicyclic hydrocarbon group having 7 to 13 carbon atoms which has the carboxyl group which is the raw material of the polymer can be obtained by a method described in Japanese Patent Application Laid-Open No. 259626/1996 which has already been disclosed by the present inventors. Of the (meth)acrylate monomers each having the epoxy group, for example, 3,4-epoxytricyclo[5.2.1.0$^{2,6}$]decylacrylate can be obtained by subjecting dicyclopentenyl acrylate to an epoxidizing reaction with peracetic acid in acetic acid. Similarly, 5,6-epoxy-2-norbornyl methacrylate can be obtained by subjecting 5-norbornene-2-methacrylate to an epoxidizing reaction.

A content of the polymer which is a constitutional factor of the photoresist material according to the present invention is usually in the range of 60 to 99.8 parts by weight, preferably 70 to 99 parts by weight with respect to 100 parts by weight of the total constitutional components including the polymer itself.

A photo-acid generator which can be used in the present invention is suitably a photo-acid generator which can generate an acid by the irradiation of a light of 400 nm or less, preferably in the range of 180 nm to 220 nm, and any photo-acid generator is acceptable, so long as a mixture of the photo-acid generator, the polymer of the present invention and the like can be sufficiently dissolved in an organic solvent and this solution is capable of forming a homogeneous coating film by a film formation method such as spin coat. The photo-acid generators may be used singly or in the form of a mixture of two or more thereof.

Examples of the usable photo-acid generator include derivatives of triphenylsulfonium salts, other onium salts thereof (e.g., compounds such as sulfonium salts, iodonium salts, phosphonium salts, diazonium salts and ammonium salts), 2,6-dinitrobenzyl esters [O. Nalamasu et al., "SPIE Proceeding", Vol. 2195, p. 137-151 (1994)], 1,2,3-tri(methanesulfonyloxy)benzene [Takumi Ueno et al., "Proceeding of PME'89", Kodansha, p. 413-424 (1990)], and sulfosuccinimide disclosed in Japanese Patent Application Laid-Open No. 5-134416. A content of the photo-acid generator is usually in the range of 0.2 to 30 parts by weight, preferably 1 to 1.5 parts by weight with respect to 100 parts by weight of the total constitutional components including the photo-acid generator itself.

When this content of the photo-acid generator is not less than 0.2 part by weight, a sufficient sensitivity can be obtained, and the formation of a pattern becomes easy. Conversely, if it is more than 30 parts by weight, some problems occur. For example, it is difficult to form a homogeneous coating film, and after development, a scum is easily generated.

Examples of the above-mentioned polyhydric alcohol which can be used in the present invention include, but are not limited to, ethylene glycol, glycerol, 1,2-butanediol, 1,3-butanediol, 1,4-butanediol, 2,3-butanediol, 1,2,4-butanetriol, 1,2-pentanediol, 1,4-pentanediol, 1,5-pentanediol, 2,4-pentanediol, 1,2-hexanediol, 1,5-hexanediol, 1,6-hexanediol, 2,5-hexanediol, 1,2-cyclohexanediol, 1,3-cyclohexanediol, 1,4-cyclohexanediol, 1,2-cyclohexanedimethanol, 1,4-cyclohexanedimethanol, 1,3,5-cyclohexanetrimethanol, 1,2-cyclopentanediol, 1,3-cyclopentanediol, 1,2-cyclooctanediol, 1,5-cyclooctanediol, tricyclodecanedimethanol, 2,3-norbornanediol, 2(3)-hydroxy-5,6-bis(hydroxymethyl) norbornane, 2,3-dihydroxy-5(6)-hydroxymethylnorbornane, 1,4-anhydroerythritol, L-arabinose, L-arabitol, D-cellobiose, cellulose, 1,5-decalindiol, glucose, galactose, lactose, maltose, mannose, mannitol and tris(2-hydroxyethyl) isocyanurate. A content of the polyhydric alcohol is usually in the range of 1 to 40 parts by weight, preferably 5 to 30 parts by weight with respect to 100 parts by weight of the total constitutional components including the polyhydric alcohol itself. The polyhydric alcohols may be used singly or in the form of a mixture of two or more thereof.

The photoresist material of the present invention can be prepared by dissolving the total constitutional components in a solvent so that the concentration of the total constitutional components at its use may be in the range of 5 to 40% by weight, and then filtering the resultant solution through a filter. As the preferable solvent to be used, any solvent is acceptable, so long as it can sufficiently dissolve the components of the resin, the photo acid generator and the polyhydric alcohol, and from the resultant solution, the homogeneous coating film can be formed in a manner such as spin coat. Furthermore, the solvents may be used singly or in the form of a mixture of two or more thereof.

Typical examples of the solvent include, but are not limited to, n-propyl alcohol, isopropyl alcohol, n-butyl alcohol, tert-butyl alcohol, methyl cellosolve acetate, ethyl cellosolve acetate, propylene glycol monoethyl ether acetate, methyl lactate, ethyl lactate, 2-methoxybutyl acetate, 2-ethoxyethyl acetate, methyl pyruvate, ethyl pyruvate, methyl 3-methoxypropionate, ethyl 3-methoxypropionate, N-methyl-2-pyrrolidinone, cyclohexanone, cyclopentanone, cyclohexanol, methyl ethyl ketone, 1,4-dioxane, ethylene glycol monomethyl ether, ethylene glycol monomethyl ether acetate, ethylene glycol monoethyl ether, ethylene glycol monoisopropyl ether, diethylene glycol monomethyl ether and diethylene glycol dimethyl ether.

The "fundamental" constituents of the photoresist material of the present invention are the above resins, the photo-acid generator and the solvents. If necessary, other additives may be added to the photoresist material of the present invention, and examples of the additives include an organic base, a surface active agent, a dyestuff, a basic additive, a stabilizer, an applicable improver and a dye.

Furthermore, the present invention also provides a method for forming a positive or negative pattern of the photoresist on a substrate to be worked by the use of the above-mentioned photoresist material. The method for forming the negative pattern of the present invention is shown in FIG. 1. In the first place, as shown in FIG. 1(A), the negative photoresist material of the present invention is applied onto a substrate 1 to be worked, and then prebaked at 60 to 170° C. for 30 to 240 seconds by a heating means such as a hot plate to form a resist film 2. Next, as shown in FIG. 1(B), the resist film 2 is selectively exposed by the use of an exposure device. After the exposure, the resist film 2 is subjected to a heating treatment. As a result, in an exposed region, an epoxy group causes a ring opening polymerization with the aid of the function of an acid generated from the photo-acid generator to crosslink a resin as shown in FIG. 1(C). Alternatively, when the photoresist material to which the polyhydric alcohol has been added is used, the epoxy group reacts not only with each other but also with the polyhydric alcohol by the function of the acid in the exposed region, so that the crosslinking of the resin is more promoted as compared with a case where no polyhydric alcohol is added. In the last step, as shown in FIG. 1(D), the unexposed portion on the resist film 2 is selectively dissolved and removed by an alkali developing solution such as an aqueous tetramethylammonium hydroxide (TMAH) solution to form the negative pattern.

The photoresist material of the present invention can be utilized as a novel photoresist material having a high transparency to a light of 220 nm or less and a high dry etching resistance. Moreover, when the photoresist material of the present invention is used in a photolithography step, a pattern can be formed.

Next, the present invention will be described in more detail in accordance with examples, but the scope of the present invention should not be limited at all by these examples.

EXAMPLE 1

Synthesis of 5-acryloyloxy-2,6-norbornanecarbolactone [an acrylate having the formula (1) in which $R^1$ and $R^2$ are hydrogen atoms:

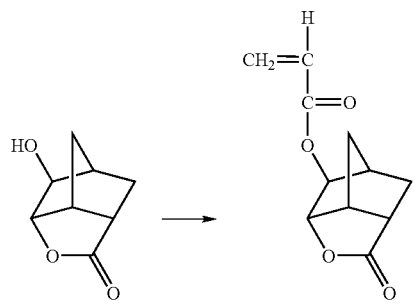

10 g (0.0653 mol) of 5-hydroxy-2,6-norbornanecarbolactone [H. B. Henbest et al., J. Chem. Soc., p. 221-226 (1959)], 9.49 g of N,N-dimethylaniline and 20 mg of phenothiazine were dissolved in 60 ml of dry THF, followed by ice-cooling. To the mixture, a solution obtained by dissolving 6.5 g of acryloyl chloride in 10 ml of dry THF was added dropwise. After stirring for 2 hours under ice-cooling and for 3 hours at room temperature, a filtrate was concentrated under reduced pressure. Afterward, 250 ml of ether were added to the resultant residue, and the solution was then washed with 200 ml of 0.5 N hydrochloric acid, saturated brine, 200 ml of an aqueous 3% NaHCO$_3$ solution, saturated brine and water in this order. The ether layer was dried over MgSO$_4$, and ether was then distilled off under reduced pressure. The precipitated white crystals were washed twice with 80 ml of hexane, thereby obtaining 5.38 g of the desired product (white solid, yield=40% and melting point=96° C.).

$^1$H-NMR (CDCl$_3$) δ 1.66 (1H, d), 1.78 (1H, d), 1.99-2.11 (2H, m), 2.53-2.62 (2H, m), 3.18-3.25 (1H, m), 4.59 (1H, d), 4.64 (1H, s), 5.89 (1H, dd), 6.11 (1H, dd), 6.43 (1H, dd); IR (KBr) 2880, 2980 (νC—H), 1712, 1773 (νC═O), 1618, 1630 (νC═C), 1186, 1205 (νC—O) cm$^{-1}$

EXAMPLE 2

Synthesis of 5-methacryloyloxy-2,6-norbornanecarbolactone [a methacrylate represented by the formula (1) wherein $R^1$ is a methyl group and $R^2$ is a hydrogen atom]:

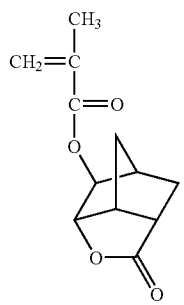

The desired product was synthesized by the same procedure as in Example 1 except that acryloyl chloride was replaced with methacryloyl chloride (yield=20%).

$^1$H-NMR (CDCl$_3$) δ 1.62 (1H, d), 1.75 (1H, d), 1.92 (3H, s), 1.95-2.16 (2H, m), 2.53-2.66 (2H, m), 3.20-3.28 (1H, m), 4.59 (1H, d), 4.65 (1H, s), 5.62 (1H, dd), 6.10 (1H, dd); IR (KBr) 2880, 2982 (νC—H), 1715, 1780 (νC=O), 1630 (νC=C), 1156, 1178 (νC—O) cm$^{-1}$

EXAMPLE 3

Synthesis of 2-methyl-6-acryloyloxy-2,6-norbornanecarbolactone [an acrylate represented by the formula (1) wherein $R^1$ is a hydrogen atom and $R^2$ is a methyl group]:

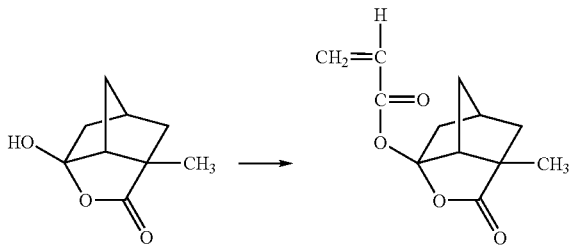

The desired product was synthesized by the same procedure as in Example 1 except that 5-hydroxy-2,6-norbornanecarbolactone was replaced with 6-hydroxy-2,6-norbornanecarbolactone [S. Beckmann et al., Chem. Ber., Vol. 94, p. 48-58 (1961)] (yield=30%).

IR (KBr) 2880, 2982 (νC—H), 1716, 1774 (νC=O), 1619, 1629 (νC=C), 1188, 1208 (νC—O) cm$^{-1}$

EXAMPLE 4

Synthesis of a polymer having the following structure [in the formula (2), $R^1$, $R^2$ and $R^3$ are hydrogen atoms; $R^4$ is a t-butoxycarbonyltetracyclo-[4.4.0.1$^{2,5}$.1$^{7,10}$]dodecyl group; and x=0.7, y=0.3 and z=0]:

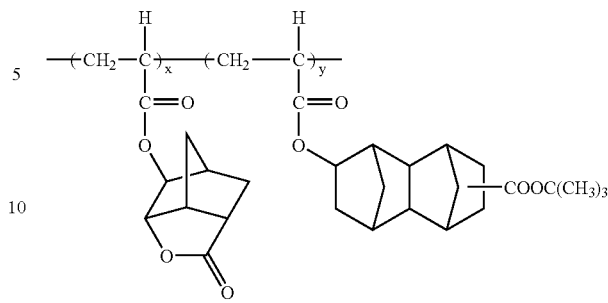

In a 100 ml round-bottom flask equipped with a reflux condenser, 2.5 g of the acrylate obtained in Example 1 and 1.71 g of t-butoxycarbonyltetracyclododecyl acrylate were dissolved in 23 ml of dry tetrahydrofuran, and to the mixture, 113 mg (30 mmol/1) of AIBN was added, followed by stirring at 60 to 65° C. under an argon atmosphere. After 2 hours, the reaction mixture was allowed to cool and then poured into 400 ml of methanol, and the deposited precipitate was collected by filtration. Furthermore, the reprecipitation/purification was carried out again to obtain 1.98 g of the desired polymer (yield=47%). In this case, a copolymerization ratio was 70:30 on the basis of an integration ratio of $^1$H-NMR (x=0.7, y=0.3). A weight-average molecular weight (Mw) of the polymer by GPC analysis was 10800 (in terms of a polystyrene), and its polydispersity (Mw/Mn) was 1.88.

EXAMPLES 5 AND 6

Polymerization was carried out in the same manner as in Example 4 except that a feed ratio of monomers was changed. Table 4 shows the feed ratios of the monomers, copolymerization ratios (x/y) of polymers, and weight-average molecular weights of the obtained copolymers.

TABLE 4

|  | Feed Ratio | x/y | Weight-Average Molecular Weight |
|---|---|---|---|
| Example 5 | 0.5/0.5 | 0.49/0.51 | 13300 |
| Example 6 | 0.35/0.65 | 0.35/0.65 | 11500 |

EXAMPLES 7 AND 8

Polymerization was carried out in the same manner as in Example 4 except that an amount (concentration) of AIBN was changed. Table 5 shows copolymerization ratios (x/y) of polymers, weight-average molecular weights of the obtained copolymers, and the like.

TABLE 5

|  | AIBN Concentration | x/y | Weight-Average Molecular Weight |
|---|---|---|---|
| Example 7 | 5 mmol/l | 0.7/0.3 | 154000 |
| Example 8 | 70 mmol/l | 0.69/0.31 | 3200 |

EXAMPLE 9

Synthesis of a polymer having the following structure [in the formula (2), $R^1$ and $R^2$ are hydrogen atoms; $R^3$ is a methyl group; R⁴ is a tetrahydropyranyloxycarbonyltetracyclo[4.4.0.1²,⁵.1⁷,¹⁰] dodecyl group; and x0.7, y=0.3 and z=0]:

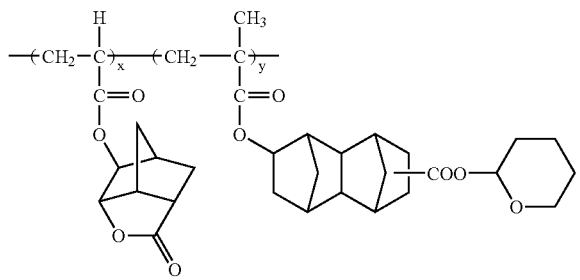

The desired polymer was synthesized by the same procedure as in Example 4 except that t-butoxycarbonyltetracyclododecyl acrylate was replaced with tetrahydropyranyloxycarbonyltetracyclododecyl methacrylate. Yield=52%, Mw=12000, and Mw/Mn=1.75.

EXAMPLE 10

Synthesis of a polymer having the following structure [in the formula (2), $R^1$ and $R^2$ are hydrogen atoms; $R^3$ is a methyl group; $R^4$ is a 2-methyl-2-adamantyl group; and x=0.7, y=0.3 and z=0]:

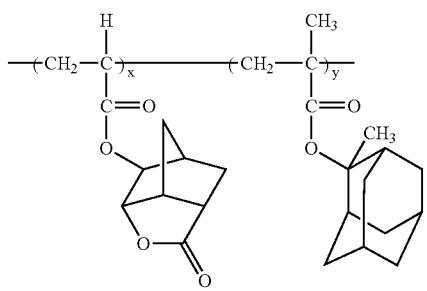

The desired polymer was synthesized by the same procedure as in Example 4 except that t-butoxycarbonyltetracyclododecyl acrylate was replaced with 2-methyl-2-adamantyl methacrylate. Yield=42%, Mw=9500, and Mw/Mn=1.96.

EXAMPLE 11

Synthesis of a polymer having the following structure [in the formula (2), $R^1$ and $R^2$ are hydrogen atoms; $R^3$ is a methyl group; $R^4$ is t-butyl methacrylate; and x=0.7, y=0.3 and z=0]:

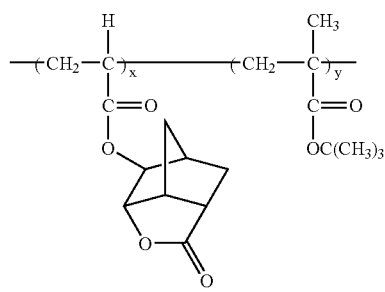

The desired polymer was synthesized by the same procedure as in Example 4 except that t-butoxycarbonyltetracyclododecyl acrylate was replaced with t-butyl methacrylate. Yield=60%, Mw=8400, and Mw/Mn=1.74.

EXAMPLE 12

Synthesis of a polymer having the following structure [in the formula (2), $R^1$, $R^2$ and $R^3$ are hydrogen atoms; $R^4$ is a t-butoxycarbonylnorbornyl group; and x=0.7, y=0.3 and z=0]:

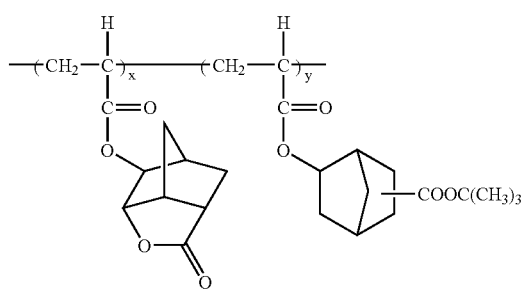

The desired polymer was synthesized by the same procedure as in Example 4 except that t-butoxycarbonyltetracyclododecyl acrylate was replaced with t-butoxycarbonylnorbornyl acrylate. Yield=44%, Mw=9100, and Mw/Mn=1.72.

EXAMPLE 13

Synthesis of a polymer having the following structure [in the formula (2), $R^1$ and $R^3$ are hydrogen atoms; $R^2$ is a methyl group; $R^4$ is a t-butoxyarbonyltetracyclo[4.4.0.1²,⁵.1⁷,¹⁰] dodecyl group; and x=0.7, y=0.3 and z=0]:

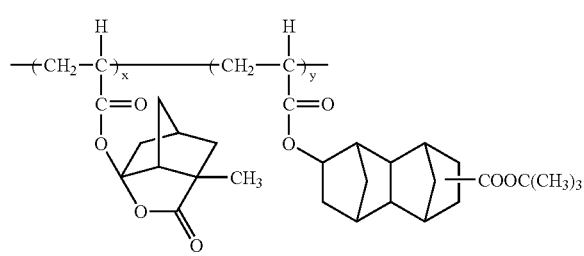

The desired polymer was synthesized by the same procedure as in Example 4 except that the acrylate obtained in Example 1 was replaced with the acrylate obtained in Example 3. Yield=60%, Mw=11300, and Mw/Mn=1.88.

EXAMPLE 14

Synthesis of a polymer having the following structure [in the formula (2), $R^1$, $R^2$ and $R^3$ are hydrogen atoms; $R^4$ is a t-butoxycarbonyltetracyclo-[4.4.0.1²,⁵.1⁷,¹⁰]dodecyl group; $R^5$ is a methyl group; $R^6$ is a hydrogen atom; and x=0.6, y=0.3 and z=0.1]:

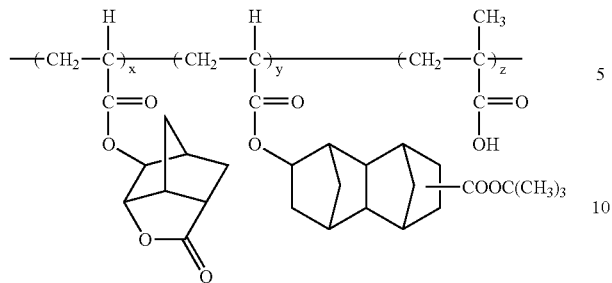

In a 100 ml round-bottom flask equipped with a reflux condenser, 3 g of the acrylate obtained in Example 1, 2.39 g of t-butoxycarbonyltetracyclododecyl acrylate and 0.207 g of methacrylic acid were dissolved in 30 ml of dry tetrahydrofuran, and to the mixture, 147 mg (30 mmol/l) of AIBN was added, followed by stirring at 60 to 65° C. under an argon atmosphere. After 2 hours, the reaction mixture was allowed to cool and then poured into 500 ml of methanol, and the deposited precipitate was collected by filtration. Furthermore, the reprecipitation/purification was carried out again to obtain 2.35 g of the desired polymer (yield=42%). In this case, a copolymerization ratio was 60:30:10 on the basis of an integration ratio of $^1$H-NMR (x=0.6, y=0.3, z=0.1). Mw=9700, and Mw/Mn=1.74.

EXAMPLE 15

Synthesis of a polymer having the following structure [in the formula (2), $R^1$, $R^2$, $R^3$ and $R^5$ are hydrogen atoms; $R^4$ is a t-butoxycarbonyltetracyclo [4.4.0.1$^{2,5}$.1$^{7,10}$]dodecyl group; $R^6$ is a tricyclodecyl group; and x=0.6, y=0.3 and z=0.1]:

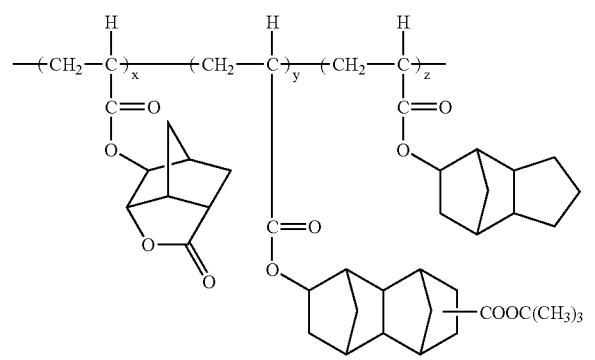

The desired polymer was synthesized by the same procedure as in Example 4 except that methacrylic acid was replaced with tricyclodecyl acrylate (trade name FA-513A, made by Hitachi Chemical Co., Ltd.). Yield=57%, Mw=13700, and Mw/Mn=2.13.

EXAMPLE 16

Synthesis of a polymer having the following structure [in the formula (2), $R^1$ and $R^2$ are hydrogen atoms; and x=1 and y=z=0]:

In a 50 ml round-bottom flask equipped with a reflux condenser, 3 g of the acrylate obtained in Example 1 were dissolved in 16 ml of dry tetrahydrofuran, and to the mixture, 79 mg (30 mmol/1) of AIBN was added, followed by stirring at 60 to 65° C. under an argon atmosphere. After 1 hour, the reaction mixture was allowed to cool and then poured into 200 ml of methanol, and the deposited precipitate was collected by-filtration. Furthermore, the reprecipitation/purification was carried out again to obtain 1.8 g of the desired polymer (yield=60%). In this case, Mw=7100 and Mw/Mn=2.05.

EXAMPLE 17

Synthesis of a polymer having the following structure [in the formula (2), $R^1$ and $R^2$ are hydrogen atoms; $R^3$ is a methyl group; $R^4$ is a 2-acetoxymenthyl group; and x=0.7, y=0.3 and z=0]:

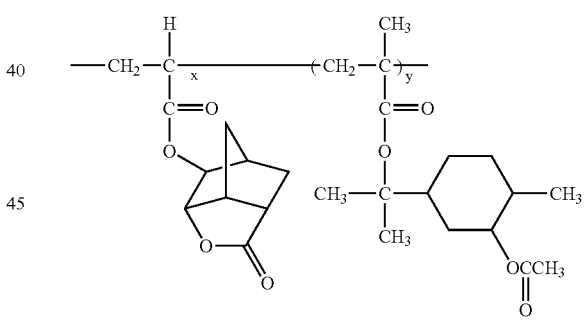

The desired polymer was synthesized by the same procedure as in Example 4 except that t-butoxycarbonyltetracyclododecyl acrylate was replaced with 2-acetoxymenthyl methacrylate (which is mentioned in Japanese Patent Application Laid-Open No. 335603/1996). Yield=52%, Mw=8600, and Mw/Mn=1.77.

EXAMPLE 18

Synthesis of a polymer having the following structure [in the formula (2), $R^1$, $R^2$, $R^3$ and $R^5$ are hydrogen atoms; $R^4$ is an epoxyethylnorbornyl group; $R^6$ is a carboxytetracyclo [4.4.0.1$^{2,5}$.1$^{7,10}$]dodecyl group; and x=0.2, y=0.47 and z=0.33]:

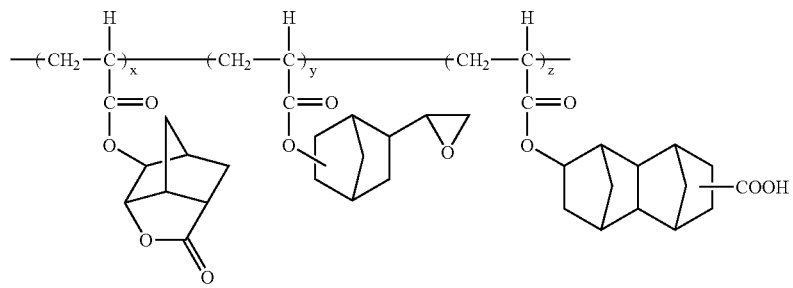

In a 100 ml round-bottom flask equipped with a reflux condenser, 2 g of the acrylate obtained in Example 1, 4.7 g of epoxyethylnorbornyl acrylate and 4.38 g of carboxytetracyclododecyl acrylate were dissolved in 60 ml of dry tetrahydrofuran, and to the mixture, 295 mg of AIBN (the monomer/AIBN=28/1) was added, followed by stirring at 60 to 65° C. under an argon atmosphere. After 2 hours, the reaction mixture was allowed to cool and then poured into 900 ml of a hexane/toluene (2/1) mixed solution, and the deposited precipitate was collected by filtration. Furthermore, the reprecipitation/purification was carried out again to obtain 5.69 g of the desired polymer (yield=51%). In this case, a copolymerization ratio was 20:47:33 on the basis of an integration ratio of $^1$H-NMR (x=0.2, y=0.47, z=0.33). A weight-average molecular weight (Mw) of the polymer by GPC analysis was 8600 (in terms of a polystyrene), and its polydispersity (Mw/Mn) was 1.45.

EXAMPLES 19, 20

Polymerization was carried out in the same manner as in Example 18 except that a feed ratio of monomers was changed. Table 6 shows the feed ratios of the monomers, copolymerization ratios (x/y/z) of polymers, and weight-average molecular weights of the obtained copolymers.

TABLE 6

|  | Feed Ratio | x/y/z | Weight-Average Molecular Weight |
|---|---|---|---|
| Example 19 | 0.1/0.65/0.25 | 0.1/0.66/0.24 | 7900 |
| Example 20 | 0.4/0.4/0.2 | 0.4/0.42/0.18 | 8300 |

EXAMPLES 21, 22

Polymerization was carried out in the same manner as in Example 18 except that an amount of AIBN (a monomer/AIBN) was changed. Table 7 shows copolymerization ratios and weight-average molecular weights of polymers.

TABLE 7

|  | Monomer/AIBN | x/y/z | Weight-Average Molecular Weight |
|---|---|---|---|
| Example 21 | 50/1 | 0.21/0.46/0.33 | 14300 |
| Example 22 | 200/1 | 0.2/0.48/0.32 | 36000 |

EXAMPLE 23

Synthesis of a polymer having the following structure [in the formula (2), $R^1$, $R^2$ and $R^3$ are hydrogen atoms; $R^4$ is an epoxyethylnorbornyl group; $R^5$ is a methyl group; $R^6$ is a hydrogen atom; and x=0.2, y=0.47 and z=0.33]:

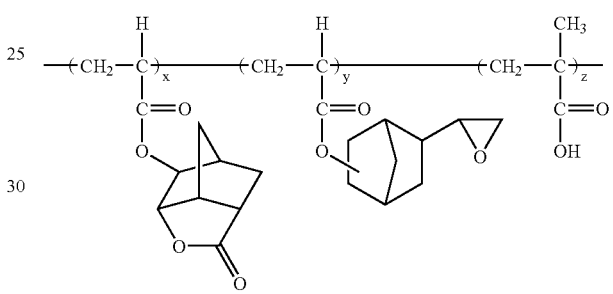

The desired polymer was synthesized by the same procedure as in Example 18 except that carboxytetracyclododecyl acrylate was replaced with methacrylic acid. Yield=61%, Mw=10800, and Mw/Mn=1.55.

EXAMPLE 24

Synthesis of a polymer having the following structure [in the formula (2), $R^1$ and $R^5$ are methyl groups; $R^2$ and $R^3$ are hydrogen atoms; $R^4$ is an epoxyethylnorbornyl group; $R^6$ is a carboxynorbornyl group; and x=0.2, y=0.47 and z=0.33]:

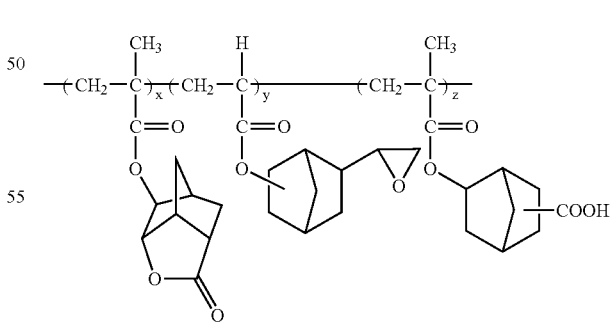

The desired polymer was synthesized by the same procedure as in Example 18 except that the monomer obtained in Example 1 was replaced with the monomer obtained in Example 2 and carboxytetracyclododecyl acrylate was replaced with carboxynorbornyl acrylate. Yield=53%, Mw=16300, and Mw/Mn=1.4.

EXAMPLE 25

Synthesis of a polymer having the following structure [in the formula (2), $R^1$, $R^2$ and $R^3$ are hydrogen atoms; $R^4$ is a 3,4-epoxytricyclo[5.2.1.0$^{2,6}$]decyl group; $R^5$ is a methyl group; $R^6$ is a carboxytetracyclo [4.4.0.1$^{2,5}$.1$^{7,10}$]dodecyl group; and x=0.2, y=0.47 and z=0.33]:

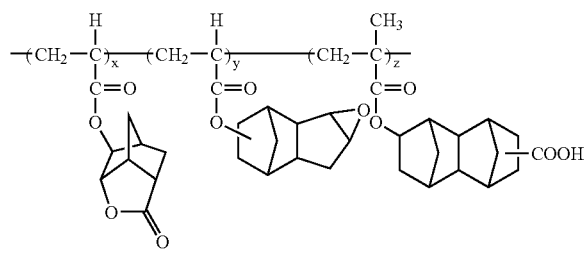

The desired polymer was synthesized by the same procedure as in Example 18 except that epoxyethylnorbornyl acrylate was replaced with 3,4-epoxytricyclo[5.2 1.0$^{2,6}$]decyl acrylate and carboxytetracyclo[4.4.0.1$^{2,5}$.1$^{7,10}$]dodecyl acrylate was replaced with carboxytetracyclo[4.4.0.1$^{2,5}$.1$^{7,10}$] dodecyl methacrylate. Yield=46%, Mw=17000, and Mw/Mn=1.5.

EXAMPLE 26

Synthesis of a polyhydric alcohol having the following structure (2,3-dihydroxy-5(6)-hydroxymethylnorbornane)

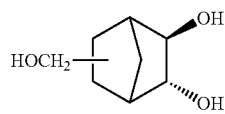

11 g of 2-hydroxymethyl-5-norboronene were dissolved in 21 ml of pyridine, and 11 ml of acetic anhydride were added dropwise to the mixture, followed by stirring at room temperature for 12 hours. The resultant reaction mixture was poured into 100 ml of water, and the organic layer was then extracted with 100 ml of ethyl acetate. Afterward, the thus extracted organic layer was washed with 0.5 N hydrochloric acid, a 3% aqueous sodium carbonate solution and saturated saline in this order. This organic layer was dried over magnesium sulfate, and ethyl acetate was distilled off under reduced pressure, thereby obtaining 13 g of 2-acetoxy-5-norbornene. Next, 13 g of 2-acetoxy-5-norbornene were added dropwise to a mixture of 50 ml of 90% formic acid and 13 ml of 30% aqueous hydrogen peroxide under ice-cooling, followed by stirring at room temperature for 12 hours. Formic acid was distilled off under reduced pressure, and 30 ml of methanol, 13 g of sodium hydroxide and 25 ml of water were added to the resultant residue and reaction was then carried out at 45 to 50° C. for 1 hour. After the reaction solution was allowed to cool, the resultant organic layer was extracted with 100 ml of ethyl acetate, washed with saturated brine, and then dried over magnesium sulfate. The solvent was distilled off under reduced pressure to obtain 5 g of 2,3-dihydroxy-5(6)-hydroxymethylnorbornane.

IR (KBr) 3380 (vO—H), 2950, 2860 (vC—H), 1050 (vC—O) cm$^{-1}$

EXAMPLE 27

(Evaluation 1 of the Etching Resistance of a Polymer)

2 g of the polymer (resin) obtained in Example 5 were dissolved in 10 g of propylene glycol monomethyl ether acetate, and then filtered through a 0.2 μm Teflon filter. Next, the filtered mixture was applied onto a 3-inch silicon substrate by spin coat, and then baked at 90° C. for 60 seconds on a hot plate to form a thin film having a thickness of 0.7 μm thereon. An etching velocity of the thus obtained film to a $CF_4$ gas was measured by the use of a DEM 451 reactive ion etching (RIE) device made by Nichiden Aneluva Co., Ltd. (etching conditions: power=100 W, pressure=5 Pa, gas flow rate=30 sccm). The results are shown in Table 8. Similarly, an etching rate of the polymer (resin) obtained in Example 15 was also measured. As comparative examples, there are also shown the results of a novolak resist (PFI-15A, made by Sumitomo Chemical Co., Ltd.), a poly(p-vinylphenol) which is used as a base resin for a KrF resist, and a poly(methyl methacrylate) coating film which is a resin not having an alicyclic hydrocarbon group in a molecular structure. Incidentally, the etching rate was normalized on the basis of the novolak resist.

TABLE 8

| | Etching rate (Relative Ratio) |
|---|---|
| Example 5 | 1.15 |
| Example 15 | 1.15 |
| Poly(methylmethacrylate) | 1.9 |
| Poly(p-vinylphenol) | 1.2 |
| Novolak Resist (PFI-15A) | 1 |

It was apparent from the above-mentioned results that the polymer (resin) of the present invention had the low etching rate to the $CF_4$ gas, and so the polymer was excellent in dry etching resistance.

EXAMPLE 28

(Evaluation 1 of the Transparency of a Polymer)

2.5 g of the polymer (resin) obtained in Example 5 were dissolved in 10 g of propylene glycol monomethyl ether acetate, and then filtered through a 0.2 μm Teflon filter. Next, the filtered mixture was applied onto a 3-inch quartz substrate by spin coat, and then baked at 90° C. for 60 seconds on a hot plate to form a thin film having a thickness of 1 μm. A transmittance of the thus obtained thin film at 193.4 nm which was a central wavelength of an ArF excimer laser light was measured by the use of an ultraviolet visible spectrophotometer. Similarly, the transmittance of the polymer (resin) obtained in Example 15 was also measured.

The transmittance of the polymer obtained in Example 5 was 54%/μm, and that of the polymer obtained in Example 15 was 55%/μm. It was confirmed from these results that the polymer of the present invention had a transparency which permitted the polymer to be utilized as a single layer resist.

EXAMPLE 29

(Evaluation 1 of the Patterning of a Resist Using a Polymer)

A resist comprising the following composition was prepared:

(a) 2 g of the polymer (Example 5)

(b) 0.02 g of a photo-acid generator [triphenylsulfonium triflate (TPS)]

(c) 11.5 g of propylene glycol monomethyl ether acetate

The mixture of the above-mentioned components was filtered through a 0.2 µm Teflon filter to prepare a resist. This resist was applied onto a 4-inch silicon substrate by spin coat, and then baked at 130° C. for 1 minute on a hot plate to form a thin film having a thickness of 0.4 µm. The thus obtained wafer having the film thereon was stilly put in a contact type exposure experimental machine sufficiently purged with nitrogen. A mask formed by depicting a pattern with chromium on a quartz plate was closely attached onto the resist film, and this film was then irradiated through the mask with an ArF excimer laser light. Afterward, the resist film was immediately baked at 110° C. for 60 seconds on the hot plate, and development was then carried out at a liquid temperature of 23° C. for 60 seconds with a 2.38% aqueous TMAH solution in accordance with an immersion method. In succession, a rinse treatment was done for 60 seconds with pure water. As a result, the exposed portion alone on the resist film was dissolved and removed with the developing solution to obtain a positive pattern. A resist using the polymer obtained in Example 15 was also evaluated in the same manner. Table 9 shows the results of sensitivity and resolution.

TABLE 9

|  | Resolution (µmL/S) | Sensitivity (mJ/cm$^2$) |
| --- | --- | --- |
| Resist Including Polymer of Example 5 | 0.19 | 6.5 |
| Resist Including Polymer of Example 15 | 0.20 | 7 |

It was apparent from the above-mentioned results that the photoresist material using the polymer of the present invention had excellent resolution properties. In addition, since a phenomenon such as pattern peeling was not observed, it could be confirmed that the photoresist material was also excellent in adhesive properties to the substrate.

EXAMPLE 30

(Evaluation 2 of the Etching Resistance of a Polymer)

2 g of the resin obtained in Example 18 were dissolved in 10 g of ethyl lactate, and then filtered through a 0.2 µm Teflon filter. Next, the filtered mixture was applied onto a 3-inch silicon substrate by spin coat, and then baked at 90° C. for 60 seconds on a hot plate to form a thin film having a thickness of 0.7 µm. An etching velocity of the thus obtained film to a $CF_4$ gas was measured by the use of a DEM 451 reactive ion etching (RIE) device made by Nichiden Aneluva Co., Ltd. (etching conditions: power=100 W, pressure=5 Pa, gas flow rate=30 sccm). The results are shown in Table 10. Similarly, an etching rate of the resin obtained in Example 25 was also measured. As comparative examples, there are also shown the results of a novolak resist (PFI-15A, made by Sumitomo Chemical Co., Ltd.), a poly(p-vinylphenol) which is used as a base resin for a KrF resist, and a poly(methyl methacrylate) coating film which is a resin not having an alicyclic hydrocarbon group in a molecular structure. Incidentally, the etching rate was normalized on the basis of the novolak resist.

TABLE 10

|  | Etching rate (Relative Ratio) |
| --- | --- |
| Example 18 | 1.1 |
| Example 25 | 1.05 |
| Poly(methyl methacrylate) | 1.9 |
| Poly(p-vinylphenol) | 1.2 |
| Novolak Resist (PFI-15A) | 1 |

It was apparent from the above-mentioned results that the resin of the present invention had the low etching velocity to the $CF_4$ gas, and so the polymer was excellent in dry etching resistance.

EXAMPLE 31

(Evaluation 2 of the Transparency of a Polymer)

2.5 g of the resin obtained in Example 18 were dissolved in 10 g of ethyl lactate, and then filtered through a 0.2 µm Teflon filter. Next, the filtered mixture was applied onto a 3-inch quartz substrate by spin coat, and then baked at 90° C. for 60 seconds on a hot plate to form a thin film having a thickness of 1 µm. A transmittance of the thus obtained film at 193.4 nm which was a central wavelength of an ArF excimer laser light was measured by the use of an ultraviolet visible spectrophotometer. Similarly, the transmittance of the resin obtained in Example 25 was also measured.

As a result, the transmittance of the polymer obtained in Example 18 was 53%/µm, and that of the polymer obtained in Example 25 was 57%/µm. It was confirmed from these results that the polymer of the present invention had a transparency which permitted the polymer to be utilized as a single layer resist.

EXAMPLE 32

(Evaluation 2 of the Patterning of a Resist Using a Polymer)

A resist solution comprising the following composition was prepared:

(a) 2 g of the polymer (Example 18)

(b) 0.04 g of a photo-acid generator [triphenylsulfonium triflate (TPS)]

(c) 11.5 g of ethyl lactate

The mixture of the above-mentioned components was filtered through a 0.2 µm Teflon filter to prepare a resist solution. This resist solution was applied onto a 4-inch silicon substrate by spin coat, and then baked at 80° C. for 1 minute on a hot plate to form a thin film having a thickness of 0.4 µm. The thus obtained wafer having the film thereon was stilly put in a close type exposure experimental machine sufficiently purged with nitrogen. A mask formed by depicting a pattern with chromium on a quartz plate was closely attached onto the resist film, and this film was then irradiated through the mask with an ArF excimer laser light. Afterward, the resist film was immediately baked at 130° C. for 60 seconds on the hot plate, and development was then carried out at a liquid temperature of 23° C. for 60 seconds with a 2.38% aqueous TMAH solution in accordance with an immersion method. In succession, a rinse treatment was done for 20 seconds with pure water. As a result, the exposed portion alone on the resist film was dissolved and removed with the developing solution to obtain a negative pattern. A resist using the polymer obtained in Example 25 was also evaluated in the same manner. Table 11 shows the results of sensitivity and resolution.

TABLE 11

|  | Resolution (µmL/S) | Sensitivity (mJ/cm$^2$) |
| --- | --- | --- |
| Resist Including Resin of Example 18 | 0.25 | 32 |
| Resist Including Resin of Example 25 | 0.24 | 28 |

EXAMPLE 33

(Evaluation 3 of the Patterning of a Resist Using a Polymer)

A resist comprising the following composition was prepared:
(a) 2 g of the polymer (Example 18)
(b) 0.3 g of the polyhydric alcohol (Example 26)
(c) 0.04 g of a photo-acid generator (triphenylsulfonium triflate)
(c) 11.5 g of ethyl lactate Exposure, baking and a development treatment were carried out in the same manner as in Example 32, followed by the evaluation of patterning. Similarly, the evaluation was also made for a resist to which tricyclo[5.2.1.0$^{2,6}$]decanedimethanol (made by Tokyo Chemical Industry Co., Ltd.) was added as the polyhydric alcohol. Table 12 shows the results of sensitivity and resolution.

TABLE 12

|  | Resolution (μmL/S) | Sensitivity (mJ/cm$^2$) |
| --- | --- | --- |
| Resist Including Polyhydric Alcohol of Example 26 | 0.19 | 6.8 |
| Resist Including Tricyclodecanedimethanol as Polyhydric Alcohol | 0.20 | 9.4 |

It was understood from the results of Examples 32 and 33 that the negative photoresist material of the present invention had excellent resolution properties. In addition, since a phenomenon such as pattern peeling was not observed, it could be confirmed that the photoresist material was also excellent in adhesive properties to the substrate. Furthermore, it was also apparent that the sensitivity and the resolution could be improved by adding the polyhydric alcohol.

As described above, in the resin for resist of the present invention, by using a resin having an alicyclic lactone structure a negative type chemical amplification resist having not only excellent resistance for dry-etching and transparency, but also superb resolution property and good adhesiveness against substrate can be obtained, thus it is possible to form a fine pattern necessary for producing semiconductor device.

What is claimed is:

1. A polymer which is obtained by polymerizing at least one (meth)acrylate and another polymerizable compound, wherein the at least one (meth)acrylate has an alicyclic lactone structure represented by formula (4):

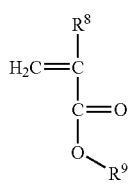

(4)

wherein R$^8$ is a hydrogen atom or a methyl group; R$^9$ is a hydrocarbon group of 7 to 16 carbon atoms having an alicyclic lactone structure.

2. A polymer of claim 1 obtained by polymerizing at least two different (meth)acrylates of formula (4).

3. A photoresist material, comprising at least one photo-acid generator and at least one polymer of claim 2.

4. A photoresist material, comprising at least one photo-acid generator and at least one polymer of claim 1.

5. A resin for resist having a solubility to an alkaline aqueous solution which increases due to the decomposition of an acid-decomposable group thereof by an action of an acid, the resin comprising at least one (meth)acrylate unit of an alicyclic lactone structure and at least one unit of another polymerizable compound, wherein the at least one unit of an alicyclic lactone structure is represented by the formula (3):

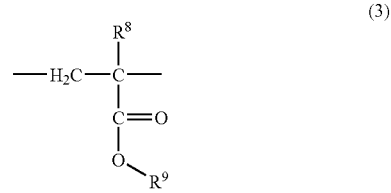

(3)

wherein R$^8$ is a hydrogen atom or a methyl group, and R$^9$ is a hydrocarbon group of 7 to 16 carbon atoms having an alicyclic lactone structure.

6. A resin for resist of claim 3, wherein the resin comprises at least two different (meth)acrylates units of an alicyclic lactone structure of formula (4).

7. A photoresist material, comprising at least one photo-acid generator and at least one resin for resist of claim 6.

8. A photoresist material, comprising at least one photo-acid generator and at least one resin for resist of claim 5.

9. A photoresist composition, comprising a substrate associated with at least one polymer which is obtained by polymerizing at least one (meth)acrylate, wherein the at least one (meth)acrylate has an alicyclic lactone structure represented by formula (4):

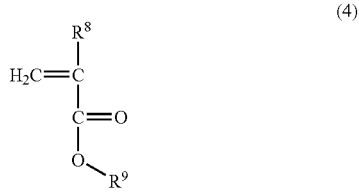

(4)

wherein R$^8$ is a hydrogen atom or a methyl group; R$^9$ is a hydrocarbon group of 7 to 16 carbon atoms having an alicyclic lactone structure.

10. A photoresist composition of claim 9, wherein the at least one polymer which is obtained by polymerizing at least one (meth)acrylate is copolymerized.

11. A photoresist composition of claim 9, wherein the at least one polymer which is obtained by polymerizing at least one (meth)acrylate is obtained by polymerizing at least two different (meth)acrylates of formula (4).

* * * * *